United States Patent [19]

Singer

[11] 4,273,572
[45] Jun. 16, 1981

[54] N-ALKYL OR ALKOXY-N'-SUBSTITUTED HYDROCARBYL UREA

[75] Inventor: Malcolm S. Singer, Novato, Calif.

[73] Assignee: Chevron Research Company, San Francisco, Calif.

[21] Appl. No.: 68,039

[22] Filed: Aug. 20, 1979

Related U.S. Application Data

[60] Division of Ser. No. 919,016, Jun. 26, 1978, Pat. No. 4,200,450, which is a division of Ser. No. 741,422, Nov. 12, 1976, Pat. No. 4,111,683, which is a continuation-in-part of Ser. No. 591,058, Jun. 27, 1975, abandoned, which is a continuation of Ser. No. 385,521, Aug. 3, 1973, abandoned, which is a continuation-in-part of Ser. No. 124,422, Mar. 16, 1971, abandoned, and Ser. No. 124,423, Mar. 16, 1971, abandoned.

[51] Int. Cl.³ .................. A01N 57/30; C07F 9/24
[52] U.S. Cl. ............................. 71/86; 71/87; 260/938
[58] Field of Search ............... 260/938; 71/86, 87

[56] References Cited

U.S. PATENT DOCUMENTS 3,861,899  1/1975  Moser et al. ..................... 71/87

Primary Examiner—Donald G. Daus
Assistant Examiner—M. C. Eakin
Attorney, Agent, or Firm—D. A. Newell; T. G. DeJonghe; R. J. Suyat

[57] ABSTRACT

Compounds of the formula

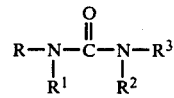

wherein R is aliphatic hydrocarbyl, alicyclic hydrocarbyl or aryl suitably substituted, if desired, or a heterocyclic group, $R^1$ is hydrogen or alkyl, $R^2$ is alkyl or alkoxy, $R^3$ is

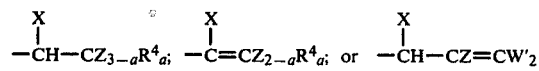

wherein a is 0 or 1, $R^4$ is hydrogen or $CW'_3$, the W' being hydrogen or halogen, Z is halogen and X is halogen, hydroxy, alkoxy, acetoxy, carbethoxyalkoxy, phenoxy, alkylthio, carbethoxyalkylthio, phenylthio, phosphono, dithiophosphonoxy, phosphoramido, isocyanato, isothiocyanato, alkyl- and dialkylthiocarbamoylthio, alkyl- and dialkylcarbamoyloxy, alkylsulfonyl, etc., have herbicidal activity.

9 Claims, No Drawings

N-ALKYL OR ALKOXY-N'-SUBSTITUTED HYDROCARBYL UREA

RELATED APPLICATIONS

This application is a division of Ser. No. 919,016, now U.S. Pat. No. 4,200,450, filed June 26, 1978, which in turn is a division of Ser. No. 741,422, now U.S. Pat. No. 4,111,683, filed Nov. 12, 1976, which in turn is a continuation-in-part of application Ser. No. 591,058, filed June 27, 1975, abandoned which, in turn, is a continuation of application Ser. No. 385,521, filed Aug. 3, 1973, now abandoned, which application is, in turn, a continuation-in-part of applications Ser. Nos. 124,422 and 124,423, both filed Mar. 16, 1971, both abandoned, the disclosures of all of which are incorporated herein by reference.

BACKGROUND OF THE INVENTION

1. Field

The present invention is concerned with ureas having herbicidal activity. Particularly, the present invention is concerned with 1-alkyl or 1-alkoxy-1-(1-substituted aliphatic hydrocarbyl)-3-substituted hydrocarbyl ureas and their use as herbicides.

2. Prior Art

U.S. Pat. No. 3,040,802 discloses beta-polyhaloalpha-hydrocarbyl isocyanates and derivatives thereof, such as 1-(1-hydroxy-2,2,2-trifluoroethyl)-3-phenyl urea and 1-(1-hydroxy-2,2,2-trichloroethyl)-3-phenyl urea, and their use as herbicides. Hoover et al, J. Org. Chem. 28(7), 1825–30 (1963) disclose compounds such as 1-(1-hydroxy-2,2,2-trifluoro-1-chloroethyl)-3-phenyl urea. Chattaway et al, Proc. Roy. Soc. (London) A-134, pages 372-84 (1931) and Chattaway et al, J. Chem. Soc. 1933, 30, disclose compounds prepared by the condensation of chloral with tolyl and nitrophenyl ureas. Also, U.S. Pat. Nos. 2,846,399, 2,902,356, 3,418,334 and 3,488,376 disclose ureas and their uses.

DESCRIPTION OF THE INVENTION

Compounds of the present invention may be represented by the formula

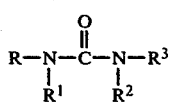
(I)

wherein R is an aliphatic hydrocarbyl group of 1 to 12 carbon atoms substituted with 0 to 4 halogen atoms of atomic number 17 to 35 (chlorine or bromine), an alicyclic hydrocarbyl group of 3 to 8 carbon atoms substituted with 0 to 4 halogen atoms of atomic number 17 to 35, an aryl group of 6 to 12 carbon atoms substituted with 0 to 5 halogen atoms of atomic number 9 to 35 (fluorine, chlorine or bromine), nitro, alkyl of 1 to 4 carbon atoms, alkoxy of 1 to 4 carbon atoms, alkylthio of 1 to 4 carbon atoms, or 0 to 1 alkylsulfoxy of 1 to 4 carbon atoms, alkylsulfonyl of 1 to 4 carbon atoms, trifluoromethyl, phenoxy, phenylthio, phenylsulfoxy, phenylsulfonyl, the phenoxy, phenylthio, phenylsulfoxy or phenylsulfonyl being substituted on the aromatic nucleus with 0 to 5 halogens of atomic number 9 to 35 or alkyl of 1 to 4 carbon atoms; or a heterocyclic group of 5 to 6 atoms containing 1 to 2 heteroatoms of oxygen, sulfur or nitrogen and being attached to the urea nitrogen through a carbon atom; $R^1$ is hydrogen or alkyl of 1 to 4 carbon atoms, $R^2$ is alkyl of 1 to 4 carbon atoms or alkoxy of 1 to 4 carbon atoms and $R^3$ is

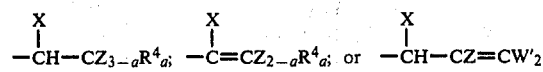

wherein a is 0 to 1 and $R^4$ is hydrogen or $CW'_3$, $W'$ representing hydrogen or halogen of atomic number 9 to 35, Z is halogen of atomic number 9 to 35, and X is (1) —$U'R^5$ wherein $U'$ is O or S, $R^5$ is hydrogen, alkyl of 1 to 4 carbon atoms substituted with 0 to 4 halogen atoms of atomic number 9 to 35, phenyl substituted with 0 to 4 halogen atoms of atomic number 9 to 35, nitro, alkyl of 1 to 4 carbon atoms, or alkoxy of 1 to 4 carbon atoms, with the proviso that when $R^5$ is hydrogen, $U'$ is S;

(2) —$P(O)(OR^6)_2$, wherein $R^6$ is alkyl of 1 to 4 carbon atoms;

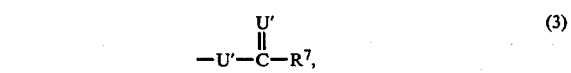
(3)

wherein $R^7$ is hydrogen or alkyl of 1 to 4 carbon atoms substituted with 0 to 4 halogen atoms of atomic number 9 to 35, or an amino group optionally substituted with 1 to 2 alkyl groups individually of 1 to 4 carbon atoms or 1 aryl group, and $U'$ is as defined above;

(4) —N=C=U', wherein U' is as defined above;

(5)

wherein $U'$ and $R^6$ are as defined above;

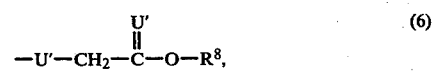
(6)

wherein $R^8$ is alkyl of 1 to 4 carbon atoms substituted with 0 to 4 halogen atoms of atomic number 9 to 35 and $U'$ is as defined above;

(7)

wherein $R^6$ is as defined above;

(8)

wherein $U'$ and $R^6$ are as defined above;

(9) fluorine, chlorine, bromine, iodine; or

(10) hydroxy.

Preferably R is alkyl of 1 to 12 carbon atoms, optionally substituted with halogen atoms, cycloalkyl of 3 to 8 carbon atoms, preferably 5 to 6 carbon atoms optionally substituted with halogen atoms or phenyl optionally substituted with halogen, nitro, alkyl, alkoxy, alkylthio, alkylsulfoxy, alkylsulfonyl, trifluoromethyl, phenoxy, phenylthio, phenylsulfoxy, phenylsulfonyl, the phenoxy, phenylthio, phenylsulfoxy, or phenylsulfonyl being optionally substituted on the aromatic nucleus with halogen or alkyl. The substituents, alkylsulfoxy, alkylsulfonyl, phenoxy, phenylthio, phenylsulfoxy or phenylsulfonyl optionally substituted on the aromatic nucleus, as the case may be, are preferably attached to the phenyl group in the p-position. The trifluoromethyl group is preferably attached to the phenyl group in the o-position. It is particularly preferred that the total number of substituents on the aryl group (or phenyl group) not exceed 2 and that when one of the substituents is alkylsulfoxy, alkylsulfonyl, trifluoromethyl, phenoxy, phenylthio, phenylsulfoxy or phenylsulfonyl that the other substituent, if any, be halogen, nitro or alkyl.

The preferred compounds of the present invention may thus be represented by the formula

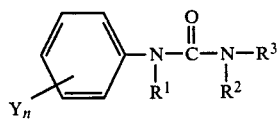
(II)

wherein $R^1$, $R^2$ and $R^3$ are as described above and Y is halogen of atomic number 9 to 35, nitro, alkyl of 1 to 4 carbon atoms, alkoxy of 1 to 4 carbon atoms, alkylthio of 1 to 4 carbon atoms, alkylsulfoxy of 1 to 4 carbon atoms, alkylsulfonyl of 1 to 4 carbon atoms, trifluoromethyl, phenoxy, phenylthio, phenylsulfoxy, phenylsulfonyl, the phenoxy, phenylthio, phenylsulfoxy or phenylsulfonyl being substituted on the aromatic nucleus with 0 to 5 halogen atoms of atomic number 9 to 35 or alkyl of 1 to 4 carbon atoms and n is 0 to 5 when Y is halogen, nitro, alkyl, alkoxy or alkylthio, and 0 to 1 when Y is alkylsulfoxy, alkylsulfonyl, trifluoromethyl, phenoxy, phenylthio, phenylsulfoxy or phenylsulfonyl. Preferably Y in the above formula (II) is halogen of atomic number 9 to 35 (fluorine, chlorine or bromine), more preferably fluorine or chlorine, alkyl of 1 to 2 carbon atoms, alkoxy of 1 to 2 carbon atoms or trifluoromethyl, and n is preferably 0 or an integer from 1 to 2.

In the above formula, $R^1$ is preferably hydrogen and $R^2$ is preferably alkyl of 1 to 4 carbon atoms, more preferably methyl.

Preferably $R^3$ in the above formula is

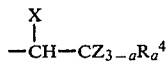

wherein A is 0 to 1 and $R^4$, X and Z are as defined above. More preferably $R^4$ is hydrogen, trichloromethyl, trifluoromethyl or methyl and Z is fluorine, chlorine or bromine. Still more preferably, a is 0 and Z is fluorine, chlorine or bromine.

Thus the particularly preferred compounds of the present invention may be represented by the formula

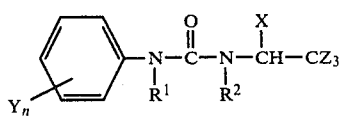
(III)

wherein $R^1$, $R^2$, Y, n, X and Z are as defined above. In particular, n will be from 1 to 2 and Y will be fluorine, chlorine or bromine, particularly fluorine in the o-position, chlorine in the o-, m- or p-position and the bromine in the p-position.

Preferably $R^5$ is hydrogen, methyl, ethyl or phenyl, $R^6$ is methyl or ethyl, $R^7$ is hydrogen, methyl or ethyl or an amino group substituted with at least one alkyl group of 1 to 2 carbon atoms (methyl or ethyl) and $R^8$ is methyl or ethyl.

More particularly, it is preferred that when X is either

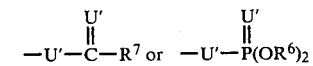

that both U's in the radical represent the same atom, that is, either oxygen or sulfur.

The most preferred compounds of formula (III) are those wherein X is halogen, especially fluorine, chlorine, or alkylthio, especially methylthio. Compounds with X equal to fluorine are preferred in part because of their stability.

Representative groups which R may represent include:
methyl,
ethyl,
n-propyl,
isopropyl,
n-butyl,
isobutyl,
sec.butyl,
decyl,
dodecyl,
chloromethyl,
chloroethyl,
cyclopropyl,
cyclobutyl,
cyclopentyl,
cyclohexyl,
phenyl,
naphthyl,
2-fluorophenyl,
2-chlorophenyl,
2-chloro-4-bromophenyl,
3-methylphenyl,
4-methoxyphenyl,
2-nitrophenyl,
4-methylthiophenyl,
4-methylsulfoxyphenyl,
4-methylsulfonylphenyl,
2-trifluoromethylphenyl,
4-phenoxyphenyl,
4-phenylthiophenyl,
4-phenylsulfoxyphenyl,
4-phenylsulfonylphenyl,
4-(2-chlorophenoxy)phenyl,
3-methyl-4-phenylthiophenyl,
thiazolyl,
pyridyl,
pyrimidyl,
oxazolyl,
isothiazolyl,
furyl, and
thienyl.

Representative groups which $R^1$ may represent include: hydrogen, methyl, ethyl, n-propyl, isopropyl, etc.

Representative groups which $R^2$ may represent include:
methyl,
ethyl, n-propyl,
isopropyl,
n-butyl,
isobutyl,
methoxy,
ethoxy, etc.

Representative groups which $R^3$ may represent include:
1-methoxy-2,2,2-trifluoromethyl,
1-methylthio-2,2-dibromo-2-chloroethyl,
1-acetoxy-2,2-dichloro-3,3-bromopropyl,
1-phenoxy-2-bromo-2-chlorovinyl,
1-ethoxy-2,3-dibromo-3,3-difluoropropyl,
1-methoxy-2,3,3-trichloro-2-propenyl, etc.

Representative groups which $R^4$ may represent include:
trifluoromethyl,
difluoromethyl,
dichloromethyl,
fluorochloromethyl, etc.

Representative groups which X may represent include:
fluorine,
chlorine,
bromine,
iodine,
hydroxy,
methoxy,
ethoxy,
chloromethoxy,
methylthio,
phenoxy,
2-chlorophenoxy,
3-nitrophenoxy,
4-methoxyphenylthio,
dimethylphosphono,
diethylphosphono,
methylethylphosphono,
acetoxy,
propionoyloxy,
chloracetoxy,
methylcarbamolyoxy,
ethylcarbamoyloxy,
dimethylcarbamoyloxy,
methyl thiocarbamoylthio,
isocyanato,
isothiocyanato,
O,O-dimethylphosphoramido,
O,O-dimethylthiophosphoramido,
carbmethoxymethylthio,
methylsulfonyl,
ethylsulfonyl, etc.

Representative compounds of the present invention include:
1-methyl-1-(1-hydroxy-2,2,2-trichloroethyl)-3-phenyl urea,
1-ethyl-1-(1-hydroxy-2,2,2-trifluoroethyl-3-(2-chlorophenyl) urea,
1-methyl-1-(1-hydroxy-2,2,2-tribromoethyl)-3-(2-fluorophenyl) urea,
1-methoxy-1-(1-hydroxy-2,2,-dichloro-2-fluoroethyl)-3-(2-nitrophenyl) urea,
1-methyl-1-(1-hydroxy-2,2-dichloroethyl)-3-(4-methylphenyl) urea,
1-butyl-1-(1-hydroxy-2,2,2-trifluoroethyl)-3-(4-methoxyphenyl) urea,
1-ethoxy-1-(1-hydroxy-2,2,2-tribromoethyl)-3-methyl-3-(3,4-dichlorophenyl) urea,
1-methyl-1-(1-hydroxy-2,2,3,3,3,-pentachloropropyl)-3-phenyl urea,
1-ethyl-1-(1-hydroxy-2,2-dichloro-3,3-difluoropropyl)-3-pentachlorophenyl urea,
1-methyl-1-(1-hydroxy-2,2-dichloropropyl)-3-(2-chloro-4-methoxyphenyl) urea,
1-methyl-1-(1-hydroxy-2,3,3-trichloro-1-propenyl)-3-(2-nitrophenyl) urea,
1-methyl-1-(1-hydroxy-2-chloro-1-propenyl)-3-(2,4,6-trichlorophenyl) urea,
1-methyl-1-(1-hydroxy-2,2,2-trichloroethyl)-3-(4-phenoxyphenyl) urea,
1-methyl-1-(1-hydroxy-2,3,3,3-tetrachloro-1-propenyl)-3-(2-fluorophenyl) urea,
1-methyl-1-(1-hydroxy-2,2,2-tribromoethyl)-3-(4-[2'-chlorophenoxy]phenyl) urea,
1-methyl-1-(1-hydroxy-2,2,2-trifluoroethyl)-3-(3-trifluoromethylphenyl) urea,
-1-methyl-1-(1-hydroxy-2-chloro-2-propenyl)-3-(3-chlorophenyl) urea,
1-methyl-1-(1-hydroxy-2,2,3,3-tetrachloropropyl)-3-(2-trifluoromethylphenyl) urea,
1-methyl-1-(1-hydroxy-2,2-dichlorovinyl)-3-(3-trifluoromethylphenyl) urea,
1-methyl-1-(1-hydroxy-2,2,2-trichloroethyl)-3-methyl urea,
1-methyl-1-(1-hydroxy-2,2,2-trichloroethyl)-3-ethyl urea,
1-methyl-1-(1-hydroxy-2,2,2-trichloroethyl)-3-dodecyl urea,
1-methyl-1-(1-hydroxy-2,2,2-trichloroethyl)-3-cyclopentyl urea,
1-methyl-1-(1-hydroxy-2,2,2-trichloroethyl)-3-cyclohexyl urea,
1-methyl-1-(1-hydroxy-2,2,2-trichloroethyl)-3-(2-thiazolyl) urea,
1-methyl-1-(1-hydroxy-2,2,2-trichloroethyl)-3-(4-thiazolyl) urea,
1-ethyl-1-(1-hydroxy-2,2,2-trichloroethyl)-3-(2-pyridyl) urea,
1-ethyl-1-(1-hydroxy-2,2,2-trichloroethyl)-3-(3-pyridyl) urea,
1-methyl-1-(1-hydroxy-2,2,2-trichloroethyl)-3-(2-pyrimidyl) urea,
1-methyl-1-(1-hydroxy-2,2,2-trichloroethyl)-3-(5-pyrimidyl) urea,
1-methyl-1-(1-hydroxy-2,2,2-trichloroethyl)-3-(2-furyl) urea,
1-methyl-1-(1-hydroxy-2,2,2-trichloroethyl)-3-(4-methylthiophenyl) urea,
1-methyl-1-(1-hydroxy-2,2,2-trichloroethyl)-3-(4-methylsulfoxyphenyl) urea,
1-methyl-1-(1-hydroxy-2,2,2-trichloroethyl)-3-(4-methylsulfonylphenyl) urea,
1-methyl-1-(1-hydroxy-2,2,2-trichloroethyl)-3-(4-phenoxyphenyl) urea,
1-ethoxy-1-(1-hydroxy-2,2,2-tribromoethyl)-3-(4-phenoxyphenyl) urea,
1-methyl-1-(1-hydroxy-2,2,3,3,3-pentachloropropyl)-3-(2-chloro-4-[2'-chlorophenoxy]phenyl) urea,
1-methyl-1-(1,2,2,2-tetrachloroethyl)-3-phenyl urea,
1-ethyl-1-(1,2,2,2-tetrachloroethyl)-3-(4-chlorophenyl) urea,
1-methyl-1-(1-chloro-2,2,2-trifluoroethyl)-3-(2,4-difluorophenyl) urea,
1-methyl-1-(1-bromo-2,2,2-trichloroethyl)-3-(2,3,4-trinitrophenyl) urea, 1-methyl-1-(1-iodo-2,2,2-trichloroethyl)-3-(2-fluorophenyl) urea,
1-methoxy-1-(1-chloro-2,2,2-tribromoethyl)-3-(2-trifluoromethylphenyl) urea,
1-ethoxy-1-(1,2,2,3-tetrachloropropyl)-3-(2-fluorophenyl) urea,
1-methyl-1-(1,2,2-trichloro-3,3,3-trifluoropropyl)-3-(3,5-dichlorophenyl) urea,
1-methyl-1-(1,2,3-trichloro-1-propenyl)-3-(2-chlorophenyl) urea,
1-methyl-1-(1,2,2-trichloropropyl)-3-(3-methyl-4-methoxyphenyl) urea,
1-methyl-1-(1,2,3,3-tetrachloro-2-propenyl)-3-(2,3,4-trichlorophenyl) urea,
1-methyl-1-(1,2,2-trifluoroethyl)-3-(4-methoxyphenyl) urea,
1-ethyl-1-(1,2-dichloro-2,2-dibromoethyl)-3-(3-chloro-4-bromophenyl) urea,
1-methyl-1-(1,2,2-trichloroethyl)-3-(4-phenoxyphenyl) urea,
1-methyl-1-(1,2,2-trichloro-2-bromoethyl)-3-(4-[4'-chlorophenoxy]phenyl) urea,
1-ethyl-1-(1-chloro-2,2,2-tribromoethyl)-3-(4-phenylsulfoxyphenyl) urea,
1-methyl-1-(1,2,2-trichlorovinyl)-3-(4-phenylsulfonylphenyl) urea,
1-methyl-1-(1-methoxy-2,2,2-trichloroethyl)-3-(2-fluorophenyl) urea,
1-methyl-1-(1-ethoxy-2,2,2-tribromoethyl)-3-(2-chlorophenyl) urea,
1-methyl-1-(1-methylmercapto-2,2,2-trichloroethyl)-3-(2,4-dichlorophenyl) urea,
1-methyl-1-(1-chloromethylmercapto-2,2,2-trifluoroethyl)-3-(4-methoxyphenyl) urea,
1-methyl-1-(1-butoxy-2,2,2-tribromoethyl)-3-(4-isopropoxyphenyl) urea,
1-butyl-1-(1-[2'-bromoethoxy]-2,2-dichloropropyl)-3-(2-trifluoromethylphenyl) urea,
1-methyl-1-(1-phenoxy-2-bromo-2,2-dichloroethyl)-3-(3-chloro-4-bromophenyl) urea,
1-methyl-1-(1-[2-fluorophenoxy]-2-bromo-3,3-dichloro-2-propenyl)-3-(2,4-dichlorophenyl) urea,
1-methyl-1-(1,2,2,2-tetrachloroethyl)-3-(2,6-dimethyl-4-methylsulfonylphenyl) urea,
O,O-dimethyl 1-(N-methyl-N-2-fluorophenylcarbamoylamino)-2,2,2-trichloroethyl phosphonate,
O,O-diethyl 1-(N-methyl-N-3-chlorophenylcarbamoylamino)-2,2,2-trifluoroethyl phosphonate,
O,O-dibutyl 1-(N-ethyl-N-2,4-dinitrophenylcarbamoylamino)-2-bromo-2,2-dichloroethyl phosphonate,
O-methyl-O-ethyl 1-(N-methyl-N-4-phenoxyphenylcarbamoylamino)-2,2,2-tribromethyl phosphonate,
O,O-diethyl 1-(N-methoxy-N-2,3,5,6-tetrachlorophenylcarbamoylamino)-2,2-dichlorovinyl phosphonate,
O,O-diethyl 1-(N-methyl-N-4-ethoxyphenylcarbamoylamino)-2,2-dichloroethyl phosphonate,
O,O-diethyl 1-(N-methyl-N-3-chloro-4-bromophenylcarbamoylamino)-2,2,3,3-tetrachloropropyl phosphonate,
1-methyl-1-(1-acetoxy-2,2,2-trichloroethyl)-3-(2,4-dichlorophenyl) urea,
1-methyl-1-(1-propionyloxy-2,2,2-trifluoroethyl)-3-(3,4-dichlorophenyl) urea,
1-methyl-1-(1-chloroacetoxy-2-bromo-2,2-dichloroethyl)-3-(3,5-dichlorophenyl) urea,
1-methyl-1-(1-dithioacetoxy-2,2,2-trichloroethyl)-3-(2-fluorophenyl) urea,
1-(N-methyl-N-2,4-dichlorophenylcarbamoylamino)-2,2,2-trichloroethyl-N',N'-dimethyldithiocarbamate,
1-methyl-1-(1-N-methylcarbamoyloxy-2,2,2-trichloroethyl)-3-(2-fluorophenyl) urea,
1-methyl-1-(1-isocyanato-2,2,2-trichloroethyl)-3-(2,4-difluorophenyl) urea,
1-methyl-1-(1-isothiocyanato-2-bromo-2,2-dichloroethyl)-3-(2-trifluoromethylphenyl) urea,
1-methyl-1-(1-isocyanato-2,2,2-trifluoroethyl)-3-phenyl urea,
1-methoxy-1-(1-isocyanato-2,2,3,3-tetrachloropropyl)-3-(3-chloro-4-bromophenyl) urea,
N-[1-(N'-2-fluorophenylcarbamoyl-N'-methylamino)-2,2,2-trichloroethyl] O,O-dimethylthiophosphoramide,
N-[1-(N'-2,4-methoxyphenylcarbamoyl-N'-methylamino)-2-bromo-2,2-dichloroethyl] O,O-diethylphosphoramide,
N-[1-(N'-phenylcarbamoyl-N'-ethylamino)-2,2-dichloro-3,3-difluoropropyl] O,O-dimethylthiophosphoramide,
N-[1-(N'-2-nitrophenylcarbamoyl-N'-methoxyamino)-2-bromo-2-chloropropyl] O,O-diethylphosphoramide,
1-methyl-1-(1-carbmethoxymethylthio-2,2,2-trichloroethyl)-3-(2-fluorophenyl) urea,
1-methyl-1-(1-carbethoxymethylthio-2-bromo-2,2-dichloroethyl)-3-(3-chlorophenyl) urea,
1-methyl-1-(1-carbmethoxymethylthio-2,2-dichloro-3,3,3-trifluoropropyl)-3-(2,4-dichlorophenyl) urea,
1-methoxy-1-(1-chlorocarbmethoxymethylthio-2,2,2-tribromoethyl)-3-(4-methylphenyl) urea,
O,O-dimethyl S-[1-(N-3-chlorophenylcarbamoyl-N-methylamino)-2,2,2-trichloroethyl] dithiophosphate,
O,O-diethyl S-[1-(N-2-fluorophenylcarbamoyl-N-methylamino)-2-bromo-2,2-dichloroethyl] thiophosphate,
O,O-dimethyl O-[1-(N-3-chloro-4-bromophenylcarbamoyl-N-ethylamino)-2,2,3,3,3-pentachloropropyl] thiophosphate
O,O-diethyl S-[1-(N-4-phenoxyphenylcarbamoyl-N-methylamino)-2,2,2-trifluoroethyl] dithiophosphate,
O,O-dimethyl S-[1-(N-2-trifluoromethylphenylcarbamoyl-N-methoxyamino)-2,2-dichloro-3,3,3-trifluoropropyl] dithiophosphate,
1-methyl-1-(1-methylsulfonyl-2,2,2-trichloroethyl)-3-(2-fluorophenyl urea,
1-ethyl-1-(1-ethylsulfonyl-2,3,3-trichloro-1-propenyl)-3-(2,4-dichlorophenyl) urea,
1-methyl-1-(1-methylsulfonyl-2,2,2-trichloroethyl)-3-(5-pyrimidyl) urea.

The compounds of the present invention wherein X is OH and $R^3$ is

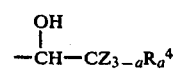

are prepared by reacting a urea with an aldehyde according to the following equation:

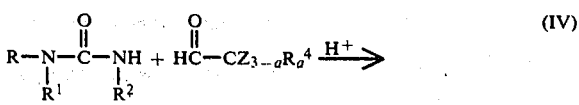

-continued

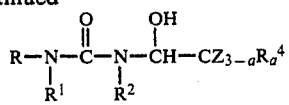

wherein R, $R^1$, $R^2$, Z, $R^4$ and a are as defined above.

The urea reactants are known compounds of the prior art. The aldehyde may be compounds such as chloral (trichloroacetaldehyde), pentachloropropinoylaldehyde, dichloroacetaldehyde, dichlorobromoacetaldehyde, etc. The reaction (IV) may be accomplished in the presence of a solvent or neat. Generally, stoichiometric amounts of the urea and aldehyde will be used. A small amount of acid, preferably sulfuric acid or perchloric acid, may be used. The reaction temperature will be from 20° to 100° C. Generally the reaction proceeds very rapidly and will be complete in a matter of a few minutes. Reaction times of from 30 seconds to 10 hours are considered sufficient.

The alpha-hydroxy compound is converted to the alpha-chloro compound (i.e., wherein X is chlorine) by reacting the product of reaction (IV) either in purified form or in the reaction mixture of reaction (IV) with thionyl chloride according to the following equation:

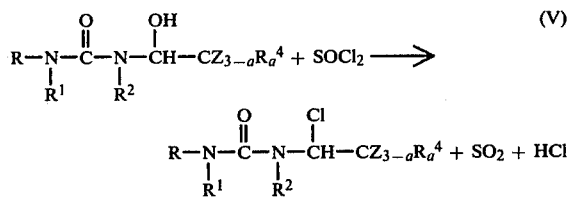
(V)

wherein R, $R^1$, $R^2$, Z, $R^4$ and a are as defined above.

The reaction (V) can be accomplished by using from a molar amount of thionyl chloride to an excess of as much as 20 mols based on the urea. The reaction temperature will be from 20° to 100° C. and reaction time will be from 1 to 20 hours. If desired, reactions (IV) and (V) may be combined to prepare the product of reaction (V) by simply mixing the urea reactant of reaction (IV), the aldehyde reactant of reaction (IV) and the thionyl chloride of reaction (V). The product of reaction (V) can be recovered by slurrying in a solvent such as diethyl ether or methylene chloride, collecting the product on a filter, then properly purifying by recrystallizing from a 1:1 mixture of 1,2-dimethoxyethane and methylene chloride or from a 1:1 acetone and methylene chloride mixture.

In order to obtain the compounds wherein X is fluorine, bromine or iodine, the product of reaction (V) can be reacted with ammonium fluoride, ammonium bromide or ammonium iodide as shown in reaction (VI) below to obtain the final product:

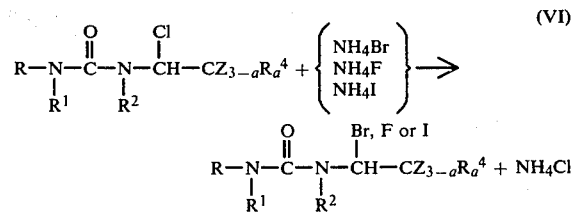
(VI)

wherein R, $R^1$, $R^2$, $R^4$, Z and a are as defined above.

The reaction (VI) may also be conducted with an alkali metal fluoride, bromide or iodide, e.g., potassium fluoride.

The above reaction (VI) can be accomplished readily be mixing the reactants preferably in a solvent such as 1,2-dimethoxyethane in an amount of from 2 to 50% for a time from 1 to 20 hours at a temperature from 20° to 100° C. The solvent is then removed and the product slurried in ether and collected. Generally the reactant in brackets will be in molar excess, in an amount from 5 to 100% of the urea reactant of reaction (VI).

The other products of the present invention can be prepared by reacting the alpha-chloro compound of reaction (V) with a variety of compounds, as shown in reaction (VII) below:

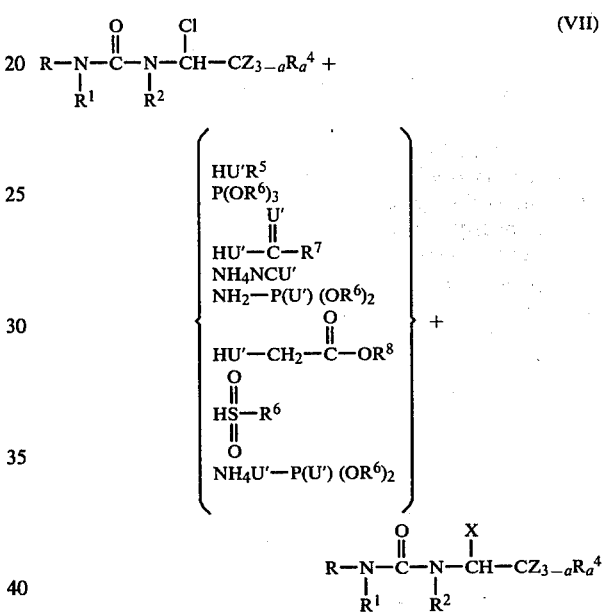
(VII)

wherein R, $R^1$, $R^2$, $R^4$, $R^5$, $R^6$, $R^7$, $R^8$, U', Z and a are as defined above.

The above reaction (VII) can be accomplished readily by mixing the reactants preferably in a solvent such as 1,2-dimethoxyethane in an amount from 2 to 50% for a time from about 0.25 to 20 hours at a temperature from about 20° to 100° C. The solvent is then removed and the product slurried in ether and collected. Generally the reactant in brackets will be in excess, in an amount of 5 to 100% of the urea reactant of reaction (VII).

In order to prepare the compounds wherein $R^3$ is

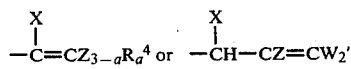

the product of reaction (VII) above is dehydrohalogenated at very mild basic conditions. The product of reaction (VII) is heated in a very mild base at a temperature from 0° to 30° C. for a period of time from 15 minutes to 2 hours to accomplish dehydrohalogenation. It is essential that the basic conditions be very mild; otherwise decomposition of the product of reaction (VII) will occur.

EXAMPLES

The present invention will be more fully understood by reference to the following examples.

EXAMPLE 1

Preparation of 1-methyl-1-(1-hydroxy)-2,2,2-trichloroethyl)-3-phenyl urea 1-methyl-3-phenyl urea (7.5 g, 0.05 mol) was reacted with 7.5 g (0.05 mol) of chloral without solvent. The mixture was shaken for a short period of time. After, 3 drops of perchloric acid were added and the mixture heated gently for a few minutes to give a homogenous viscous oil. Upon cooling, a glass formed. The chemical analysis showed: %Cl, calc. 35.8, found, 35.8; %N, calc. 9.4, found 8.0.

EXAMPLE 2

Preparation of 1-methyl-1-(1,2,2,2-tetrachloroethyl)-3-(2-fluorophenyl) urea

N-methyl-N'-o-fluorophenyl urea (16.8 g, 0.1 mol) was combined with 22.5 g (0.15 mol) chloral and 18.0 g (0.15 mol) thionyl chloride. After several minutes, an exothermicity was noted and the reaction mixture became a homogenous yellow oil. After 5 minutes more, a precipitate began to form. After 1½ hours, a 3:1 mixture of diethyl ether:petroleum ether was added and the product was collected on a filter and dried. The solid, which weighed 25 g, melted at 130°–141° C. and analyzed as follows: %Cl, calc. 35.7, found 37.3; %N, calc. 9.5, found 9.5.

EXAMPLE 3

Preparation of 1-methyl-1-1,2,2,2-tetrachloroethyl)-3-(3,4-dichlorophenyl) urea 1-(3,4-dichlorophenyl)-3-methyl urea (15.2 g, 0.07 mol) was combined with 15.0 g (0.1 mol) of chloral and 5 drops of concentrated sulfuric acid. The mixture was heated for an hour to effect reaction, then stripped under vacuum. To the crude 1-(3,4-dichlorophenyl)-3-(1-hydroxy-2,2,2-trichloroethyl)-3-methyl urea was added an excess of thionyl chloride and the mixture was heated gradually to a maximum of 65° C. Diethyl ether was added to the crude product, and the insoluble product was collected on a filter, washed twice with diethyl ether and dried. The 15.3 g of product, which melted at 132°–140° C., analyzed as follows: %Cl, calc. 55.2, found 46.0.

EXAMPLE 4

Preparation of 1-methyl-1-(1,2,2,2-tetrachloroethyl)-3-(4-phenoxyphenyl) urea p-Phenoxyaniline (11.7 g, 0.063 mol) was dissolved in 25 ml 1,2-dimethoxyethane (Ansul E-121) and heated to 65° C. Methyl isocyanate (3.7 g, 0.65 mol) was added over a period of 10 minutes. Heating and stirring were continued for 1 hour. Then chloral (14.8 g, 0.1 mol) was added to the hot solution, followed immediately by the addition of 11.9 g (0.1 mol) thionyl chloride. It was kept at 65° C. for 4½ hours. The solution was cooled to 40°, and 25 ml of methylene chloride was added. The solution was refluxed for one more hour and then allowed to cool. The solid which formed upon cooling was filtered, washed with methylene chloride to give 5.0 g (20% yield) of a white powder, melting point 165°–167° C. A second crop, melting point 160°–162° C., weighed 5.5 g (22%). Elemental analysis showed: %Cl, calc. 34.8, found 34.35; %N, calc. 6.9, found 6.8; %C, calc., 47.1, found 47.5; %H, calc. 3.46, found 3.3.

EXAMPLE 5

Preparation of 1-methyl-1-(1-methylthio-2,2,2-trichloroethyl)-3-(2-fluorophenyl) urea 1-methyl-1-(1,2,2,2-tetrachloroethyl)-3-(2-fluorophenyl) urea (16.7 g, 0.05 mol) was dissolved by heating (30°–40° C.) in 100 cc dimethoxyethane, then methylmercaptan was bubbled into the hot solution for 20 minutes. An initial exothermicity occurred, then the temperature dropped gradually to 30° C. Removal of the solvent yielded a solid, which after being slurried in ether was collected on a filter and dried. The crystalline solid, 7 g, melted at 127°–130° C. and analyzed as follows: %S, calc. 9.3, found 8.0; %Cl, calc. 30.8, found 26.9.

EXAMPLE 6

Preparation of 1-methyl-1-(1-acetoxy-2,2,2-trichloroethyl)-3-(3,4-dichlorophenyl) urea 1-methyl-1-(1,2,2,2-tetrachloroethyl)-3-(3,4-dichlorophenyl) urea (7.7 g, 0.02 mol) was dissolved in 200 ml dimethoxyethane, followed by the addition of 1.5 g of ammonium acetate. The mixture was stirred for 2 hours, filtered, and stripped of solvent. The residual mush was added to ether and the ether-insoluble material filtered off. Next, the ether was removed under vacuum. The residual oil was added to chloroform and some undissolved material was removed by filtration. The filtrate was evaporated to give 5.5 g of an oily product. The infrared and NMR spectra were consistent with the assigned structure. The chlorine analysis was: %Cl, calc. 43.5, found 41.7.

EXAMPLE 7

Preparation of 1-methyl-1-(1-isothiocyanato-2,2,2-trichloroethyl)-3-(3,4-dichlorophenyl) urea 1-methyl-1-(1,2,2,2-tetrachloroethyl)-3-(3,4-dichlorophenyl) urea (7.7 g, 0.02 mol) was dissolved in 200 ml dimethoxyethane, followed by addition of 1.5 g (0.02 mol) of ammonium thiocyanate. The mixture was stirred for 2 hours, filtered and stripped of solvent. Ether was added to the residue, which was again filtered to remove a small amount of solid. The remaining solvent was then removed, leaving a dark oil which solidified upon standing. This material had a melting point of 142°–146° C. The infrared spectrum of the material showed a broad absorption band at 4.9 micron (for the —N=C=S group). Elemental analysis showed: %Cl, calc., 43.6, found 36.7; %S, calc. 7.9, found 6.3.

Other compounds of the present invention were prepared using the methods as described above. These compounds are listed in Table I.

UTILITY

The ureas of the present invention are, in general, herbicidal in both pre- and post-emergent applications. For pre-emergent control of undesirable vegetation, these ureas will be applied in herbicidal quantities to the environment, e.g., soil infested with seeds and/or seedlings of such vegetation. Such application will inhibit the growth of or kill the seeds, germinating seeds and seedlings. For post-emergent applications, the ureas of the present invention will be applied directly to the foliage and other plant parts. Generally they are effective against weed grasses as well as broad-leaved weeds. Some may be selective with respect to type of application and/or type of weed.

Pre- and post-emergent herbicidal tests on representative ureas of this invention were made using the following methods:

Pre-Emergent Test

Acetone solutions of the test ureas were prepared by mixing 750 mg urea, 220 mg of a nonionic surfactant and 25 ml of acetone. This solution was added to approximately 125 ml of water containing 156 mg of surfactant.

Seeds of the test vegetation were planted in a pot of soil and the urea solution was sprayed uniformly onto the soil surface at a dose of 100 mg per $cm^2$. The pot was watered and placed in a greenhouse. The pot was watered intermittently and was observed for seedling emergence, health of emerging seedlings, etc., for a 3-week period. At the end of this period, the herbicidal effectiveness of the urea was rated, based on the physiological observations. A 0-to-100 scale was used, 0 representing no phytotoxicity, 100 representing complete kill.

Post-Emergent Test

The test ureas were formulated in the same manner as described above for the pre-emergent test. The concentration of the urea in this formulation was 5000 ppm. This formulation was uniformly sprayed on 2 similar pots of 24-day-old plants (approximately 15 to 25 plants per pot) at a dose of 100 mg per $cm^2$. After the plants had dried, they were placed in a greenhouse and then watered intermittently at their bases, as needed. The plants were observed periodically for phytotoxic effects and physiological and morphological responses to the treatment. After 3 weeks the herbicidal effectiveness of the urea was rated, based on these observations. A 0-to-100 scale was used, 0 representing no phytotoxicity, 100 representing complete kill.

The results of these tests appear in Table II.

The amount of urea administered will vary with the particular plant part or plant growth medium which is to be contacted, the general location of application—i.e., sheltered areas such as greenhouses as compared to exposed areas such as fields—as well as the desired type of control. For pre-emergent control of most plants, dosages in the range of about 0.5 to 20 lbs/acre will be used. Such administration will give a concentration of about 2 to 80 ppm urea distributed throughout 0.1 acre-foot. For post-emergent application, such as foliar spray application, compositions containing about 0.5 to 8 lbs urea per 100 gals spray will be used. Such application is equivalent to about 0.5 to 20 lbs urea per acre.

The herbicidal compositions of this invention comprise an herbicidal amount of one or more of the above-described ureas intimately admixed with a biologically inert carrier. The carrier may be a liquid diluent, such as water or acetone, or a solid. The solid may be in the form of dust powder or granules. These compositions will also usually contain adjuvants such as a wetting or dispersing agent to facilitate their pentration into the plant growth medium or plant tissue and generally enhance their effectiveness. These compositions may also contain other pesticides, stabilizers, conditioners, fillers, and the like.

One of the compounds of the present invention, namely 1-methyl-1-(1-hydroxy-2,2,2-trichloroethyl)-3-(3-chlorophenyl) urea, was compared with the related compound of the prior art, namely 1-(1-hydroxy-2,2,2-trichloroethyl)-3-(3-chlorophenyl) urea. The comparison was for herbicidal effectiveness, the testing procedure being substantially the same as described above. The results are shown in Table III.

TABLE I

| Compound | Halogen | | N | | S | | Melting Point, °C. |
|---|---|---|---|---|---|---|---|
| | Calc. | Found | Calc. | Found | Calc. | Found | |
| 1-methyl-1-(1-ethoxy-2,2,2-trichloroethyl-3-(2-fluorophenyl) urea | Cl 27.2<br>F 7.3 | 27.6<br>7.2 | | | | | 162–163 |
| 1-methyl-1-(1-ethoxy-2,2,2-trichloroethyl)-3-(2-chlorophenyl) urea | 38.4 | 38.8 | | | | | 124–127 |
| 1-methyl-1-(1-ethoxy-2,2,2-trichloroethyl)-3-(2-trifluoromethylphenyl) urea | Cl 22.8<br>F 18.3 | 22.6<br>18.6 | | | | | 123–127 |
| 1-methyl-1-(1-methoxy-2,2,2-trichloroethyl-3-(3-tolyl) urea | 32.6 | 30.5 | 8.6 | 8.2 | | | 133–135 |
| 1-methyl-1-(1-ethoxy-2,2,2-trichloroethyl)-3-(3-chlorophenyl) urea | 39.4 | 38.7 | 7.8 | 7.0 | | | 104–106 |
| 1-methyl-1-(1-methoxy-2,2,2-trichloroethyl)-3-(2-fluorophenyl) urea | 32.2 | 32.2 | 8.5 | 8.5 | | | 152–153 |
| 1-methyl-1-(1-methylthio-2,2,2-trichloroethyl)-3-(2-fluorophenyl) urea | 30.8 | 26.9 | | | 9.3 | 8.0 | 127–130 |
| 1-methyl-1-(1-ethylthio-2,2,2-trichloroethyl)-3-(2-fluorophenyl) urea | 29.5 | 29.1 | | | 8.9 | 8.4 | 144–147 |
| 1-methyl-1-(1-phenylthio-2,2,2-trichloroethyl)-3-(2-fluorophenyl) urea | 26.0 | 25.3 | | | 7.9 | 7.8 | 121–125 |
| 1-methyl-1-(1-methylthio-2,2,2-trichloroethyl)-3-(3-tolyl) urea | 31.1 | 30.6 | | | 9.4 | 9.8 | 132–134 |
| 1-methyl-1-(1-methylthio-2,2,2-trichloroethyl)-3-(3-chlorophenyl) urea | 39.2 | 38.5 | | | 8.8 | 9.1 | 127–130 |
| 1-methyl-1-(1-ethylthio-2,2,2-trichloroethyl)-3-(3-chlorophenyl) urea | 37.8 | 35.4 | | | 8.5 | 8.0 | 142–145 |
| 1-methyl-1-(1-ethylthio-2,2,2-trichloroethyl)-3-(3,4-dichlorophenyl) urea | 43.2 | 40.1 | | | 7.8 | 7.3 | 125–128 |
| 1-methyl-1-(1-methylthio-2,2,2-trichloroethyl)-3-(3,4-dichlorophenyl) urea | 44.7 | 41.4 | | | 8.1 | 7.4 | 151–153 |
| 1-methyl-1-(1-ethylthio-2,2,2-trichloroethyl)-3-phenyl urea | 31.1 | 30.4 | | | 9.4 | 7.9 | 155–157 |

TABLE I-continued

| Compound | Elemental Analysis | | | | | | Melting Point, °C. |
|---|---|---|---|---|---|---|---|
| | Halogen | | N | | S | | |
| | Calc. | Found | Calc. | Found | Calc. | Found | |
| O,O-diethyl 1-(N-methyl-N-2-fluorophenylcarbamoylamino)-2,2,2-trichloroethyl phosphonate | 24.5 | 22.5 | | | 7.1[1] | 7.4[1] | ≈95 |
| O,O-dimethyl 1-(N-methyl-N-3-chlorophenylcarbamoylamino)-2,2,2-trichloroethyl phosphonate | 33.5 | 34.2 | | | 7.3[1] | 7.0[1] | oil |
| O,O-dimethyl 1-[N-(3,4-dichlorophenylcarbamoyl)-N-methylamino]-2,2,2-trichloroethyl phosphonate | 38.6 | 39.0 | | | 6.8[1] | 7.0[1] | oil |
| O,O-diethyl 1-[N-(3-chlorophenylcarbamoyl)-N-methylamino]-2,2,2-trichloroethyl phosphonate | 31.4 | 28.8 | | | 6.9[1] | 6.7[1] | oil |
| 1-[N'-(2-fluorophenylcarbamoyl)-N'-methylamino]-2,2,2-trichloroethyl-N,N-dimethyl]dithio carbamate | 25.4 | 24.0 | | | 15.3 | 13.9 | 142–145 |
| 1-methyl-1-(1-acetoxy-2,2,2-trichloroethyl)-3-(3-chlorophenyl) urea | 38.0 | 34.6 | 7.5 | 7.0 | | | 150–152 |
| 1-methyl-1-(1-N-methylcarbamoyloxy-2,2,2-trichloroethyl)-3-(3-chlorophenyl) urea | 36.5 | 30.2 | 10.7 | 9.2 | | | oil |
| 1-methyl-1-(1-isothiocyanato-2,2,2-trichloroethyl)-3-(2-fluorophenyl) urea | 29.8 | 30.0 | | | 9.0 | 9.0 | 133–134 |
| N-[1-(N'-3-chlorophenylcarbamoyl-N'-methylamino)-2,2,2-trichloroethyl] O,O-dimethylthiophosphoramide | 31.2 | 25.2 | | | 7.1 | 6.7 | oil |
| N-[1-(N-{3,4-dichlorophenylcarbamoyl}-N-methylamino)-2,2,2-trichloroethyl] O,O-dimethylthiophosphoramide | 36.2 | 37.2 | | | 6.5 | 6.5 | oil |
| 1-methyl-1-(1-carbethoxymethylthio-2,2,2-trichloroethyl)-3-(3-chlorophenyl) urea | 32.7 | 31.7 | | | 7.4 | 7.0 | oil |
| 1-methyl-1-(1-carbethoxymethylthio-2,2,2-trichloroethyl)-3-(3,4-dichlorophenyl) urea | 37.8 | 34.9 | | | 6.8 | 6.9 | oil |
| 1-methyl-1-(1-carbethoxymethylthio-2,2,2-trichloroethyl)-3-(2-fluorophenyl) urea | 25.4 | 25.7 | | | 7.7 | 7.4 | oil |
| 1-methyl-1-(1-carbethoxymethoxy-2,2,2-trichloroethyl)-3-(3-chlorophenyl) urea | 34.0 | 30.3 | 6.7 | 6.5 | | | oil |
| 1-methyl-1-(1-carbethoxymethoxy-2,2,2-trichloroethyl)-3-(3,4-dichlorophenyl) urea | 39.2 | 36.7 | 6.2 | 5.4 | | | oil |
| 1-methyl-1-(1-carbethoxymethoxy-2,2,2-trichloroethyl)-3-(2-fluorophenyl) urea | Cl 26.4<br>F 4.7 | 26.6<br>4.8 | | | | | oil |
| O,O-dimethyl S-(1-[N-3-chlorophenylcarbamoyl-N-methylamino]-2,2,2-trichloroethyl)dithiophosphate | 30.1 | 26.4 | | | 13.6 | 12.7 | 148–151 |
| O,O-diethyl S-[1-(N-3,4-dichlorophenylcarbamoyl-N-methylamino)-2,2,2-trichloroethyl]dithiophosphate | 28.4 | 26.5 | | | 12.8 | 12.2 | 158–160 |
| O,O-dimethyl S-[1-(N-3,4-dichlorophenylcarbamoyl-N-methylamino)-2,2,2-trichloroethyl]dithiophosphate | 35.0 | 32.4 | | | 12.6 | 11.6 | 181–183 |
| O,O-dimethyl S-[1-(N-2-fluorophenylcarbamoyl-N-methylamino-2,2,2-trichloroethyl]dithiophosphate | 23.3 | 23.5 | | | 14.1 | 14.0 | 115–117 |
| O,O-diethyl S-[1-(N-3,4-dichlorophenylcarbamoyl-N-methylamino)-2,2,2-trichloroethyl]dithiophosphate | 33.1 | 32.6 | | | 12.0 | 11.8 | 170–173 |
| O,O-diethyl S-[N-2-fluorophenylcarbamoyl-N-methylamino)-2,2,2-trichloroethyl]dithiophosphate | 21.9 | 22.1 | | | 13.2 | 13.9 | 150–153 |
| 1-methyl-1-(1-isothiocyanato-2,2,2-trichloroethyl)-3-cyclohexyl urea | | | 12.2 | 11.5 | | | 123–124 |
| 1-methyl-1-(1-isothiocyanato-2,2,2-trichloroethyl)-3-cyclopentyl urea | 32.2 | 31.8 | | | 9.7 | 9.6 | 105–106 |
| 1-methyl-1-(1-isothiocyanato-2,2,2-trichloroethyl)-3-t-butyl urea | 33.4 | 33.5 | | | 10.1 | 10.0 | 98–101 |
| 1-methyl-1-(1-isothiocyanato-2,2,2-trichloroethyl)-3-dodecyl urea | 24.7 | 24.8 | | | 7.4 | 7.5 | 66–68.5 |
| 1-methyl-1-(1-methoxy-2,2,2-trichloro)-3-(3,4-dichlorophenyl) urea | | | 7.4 | 8.0 | 34.7[2] | 35.9[2] | 165–168 |
| 1-methyl-1-(1-methylthio-2,2,2-trichloroethyl)-3-cyclohexyl urea | | | 8.4 | 8.1 | | | 148–150 |
| 1-methyl-1-(1-methylthio-2,2,2-trichloroethyl)-3-methyl urea | 40.1 | 38.6 | | | 12.1 | 11.1 | 167–168 |
| 1-methyl-1-(1-methylthio-2,2,2-trichloroethyl)-3-cyclopentyl urea | 33.3 | 33.4 | | | 10.0 | 10.2 | 121–123 |
| 1-methyl-1-(1-methylthio-2,2,2-trichloroethyl)-3-t-butyl urea | 34.6 | 35.1 | | | 10.4 | 10.4 | 102–103 |
| 1-methyl-1-(1-methylthio-2,2,2-trichloroethyl)-3-dodecyl urea | 25.3 | 23.3 | | | 7.6 | 7.2 | 48–49 |
| 1-methyl-1-(1-methylsulfonyl-2,2,2-trichloroethyl)-3-cyclohexyl urea | 29.1 | 27.3 | | | 8.8 | 8.6 | 146–149 |
| 1-methyl-1-(1-methylsulfonyl-2,2-dichlorovinyl)-3-methyl urea | 27.2 | 29.4 | | | 12.3 | 12.1 | 170–173 |
| 1-methyl-1-(1-methylsulfonyl-2,2,2-trichloroethyl)-3-cyclopentyl urea | 30.3 | 29.3 | | | 9.1 | 9.0 | 135–138 |
| 1-methyl-1-(1-methylsulfonyl-2,2-dichlorovinyl)-3-cyclopentyl urea | 22.5 | 22.5 | | | 10.2 | 10.0 | 147.5–149 |
| 1-methyl-1-(1-methylsulfonyl-2,2,2-trichloroethyl)-3-t-butyl urea | 31.3 | 30.4 | | | 9.4 | 9.3 | 109–110 |
| 1-methyl-1-(1-N-methylcarbamoyloxy-2,2,2-trichloroethyl)-(3,4-dichlorophenyl) urea | 42.0 | 44.5 | 9.9 | 7.8 | 34.1[2] | 33.7[2] | oil |
| 1-methyl-1-(1-N-phenylcarbamoyloxy-2,2,2-trichloroethyl)-(3,4-dichlorophenyl) urea | 36.6 | 36.2 | 8.7 | 6.5 | 42.1[2] | 40.0[2] | oil |
| 1-methyl-1-(1,2,2,2-tetrachloroethyl)-3-(2-chlorophenyl) urea | 45.2 | 49.4 | | | | | 139–145 |
| 1-methyl-1-(1,2,2,2-tetrachloroethyl)-3-(4-chlorophenyl) urea | 45.2 | 41.9 | | | | | 175–180 |
| 1-methyl-1-(1,2,2,2-tetrachloroethyl)-3-(2,4-dichlorophenyl) urea | 45.5 | 43.6 | | | | | 190–193 |

TABLE I-continued

| Compound | Halogen | Calc. | Found | N Calc. | N Found | S Calc. | S Found | Melting Point, °C. |
|---|---|---|---|---|---|---|---|---|
| 1-methyl-1-(1,2,2,2-tetrachloroethyl)-3-(4-bromophenyl) urea | | 12.7[3] | 13.4[3] | | | | | 187–190 |
| 1-methyl-1-(1,2,2,2-tetrachloroethyl)-3-(3-chlorophenyl) urea | | 50.6 | 50.0 | 8.0 | 7.3 | | | 155–160 |
| 1-methyl-1-(1-chloro-2,2,2-tribromoethyl)-3-(3,4-dichlorophenyl) urea | | 11.6[3] | 11.6[3] | 5.4 | 5.5 | | | 155–158 |
| 1-methyl-1-(1,2,2,2-tetrachloroethyl)-3-phenyl urea | | 44.9 | 34.4 | 8.9 | 8.4 | | | 164–166 |
| 1-methyl-1-(1,2,2,2-tetrachloroethyl)-3-(3-chloro-4-bromophenyl) urea | | 14.0[3] | 13.7[3] | 6.5 | 6.2 | | | 189–190 |
| 1-methyl-1-(1-hydroxy-2,2,2-trichloroethyl)-3-(3-chlorophenyl) urea | | 42.8 | 39.4 | 8.4 | 9.5 | | | oil |
| 1-methyl-1-(1,2,2,2-tetrachloroethyl)-3-(2-trifluoromethylphenyl) urea | Cl F | 30.6 16.4 | 30.9 16.2 | | | | | 145–148 |
| 1-methyl-1-(1,2,2,2-tetrachloroethyl)-3-(3,5-dichlorophenyl) urea | | 55.4 | 50.3 | 7.3 | 7.5 | | | 150–157 |
| 1-methyl-1-(1,2,2-trichloro-2-bromoethyl)-3-(2-fluorophenyl) urea | | 10.6[3] | 10.5[3] | | | | | 139–142 |
| 1-methyl-1-(1-bromo-2,2,2-trichloroethyl)-3-(2-fluorophenyl) urea | Br[4] | 21.2 | 21.5 | | | | | 153–155 |
| 1-methyl-1-(1,2,2,2-tetrachloroethyl)-3-(4-methoxyphenyl) urea | | 41.1 | 40.1 | 8.1 | 8.2 | | | 176–179 |
| 1-methyl-1-(1,2,2-trichloro-2-bromoethyl)-3-(3,4-dichlorophenyl) urea | | 14.0[3] | 13.8[3] | 6.2 | 6.3 | | | 166–169 |
| 1-methyl-1-(1,2,2-trichloro-2-bromoethyl)-3-(3-chlorophenyl) urea | Cl[4] | 9.0 | 8.4 | | | | | 150–152 |
| 1-methyl-1-(1,2,2,2-tetrachloroethyl)-3-(3-trifluoromethylphenyl) urea | Cl[4] F | 9.3 14.8 | 9.2 14.9 | | | | | 138–142 |
| 1-methyl-1-(1,2-dibromo-2,2-dichloroethyl)-3-(2-fluorophenyl) urea | Br[4] | 19.5 | 16.2 | 6.8 | 7.5 | | | 130–133 |
| 1-methyl-1-(1,2,2,2-tetrachloroethyl)-3-[3-methyl-4-(4'-chlorophenylthio)phenyl] urea | | 37.5 | 35.4 | | | 6.8 | 6.8 | 152–154 |
| 1-methyl-1-(1,2,2,2-tetrachloroethyl)-3-[3-methyl-4-(4-chlorophenylsulfonyl)phenyl] urea | | 35.1 | 29.0 | | | 6.3 38.0[2] | 6.8 38.0[2] | 168–171 |
| 1-methyl-1-(1,2,2-trichloroethyl)-3-(3-chlorophenyl) urea | | | | 8.9 | 8.9 | | | 118–127 |
| 1-methyl-1-(1,2,2,2-tetrachloroethyl)-3-[4-(4'-chlorophenoxy)phenyl] urea | | 40.1 | 39.6 | 6.3 | 6.3 | | | 153–156 |
| 1-methyl-1-(1-hydroxy-2,2,2-trichloroethyl)-3-(3-pyridyl) urea | | 35.6 | 32.2 | 14.1 | 12.0 | | | oil |
| 1-methyl-1-(1-hydroxy-2,2,2-trichloroethyl)-3-(2-thiazolyl) urea | | 34.9 | 35.8 | | | | | oil |
| 1-methyl-1-(1-hydroxy-2,2,2-trichloroethyl)-3-(2-pyridyl) urea | | 35.6 | 33.6 | | | | | oil |
| 1-methyl-1-(1-hydroxy-2,2,2-trichloroethyl)-3-(2-pyrimidyl) urea | | 35.5 | 35.4 | 18.7 | 18.2 | | | 100–104 |
| 1-methyl-1-(1,2,2,2-tetrachloroethyl)-3-cyclopentyl urea | | | | 9.1 | 8.7 | | | 132–136 |
| 1-methyl-1-(1,2,2,2-tetrachloroethyl)-3-cyclohexyl urea | | | | 8.7 | 8.4 | | | 127–129.5 |
| 1-methyl-1-(1,2,2,2-tetrachloroethyl)-3-methyl urea | | | | 11.0 | 10.9 | | | 73–76 |
| 1-methyl-1-(1,2,2,2-tetrachloroethyl)-3-n-hexyl urea | | | | 8.7 | 9.2 | | | 45–55 |
| 1-methyl-1-(1,2,2,2-tetrachloroethyl)-3-t-butyl urea | | | | 9.5 | 9.7 | 32.5[2] | 31.7[2] | 84–88 |
| 1-methyl-1-(1,2,2,2-tetrachloroethyl)-3-n-dodecyl urea | | 34.7 | 33.5 | 6.9 | 6.3 | | | 39–41 |
| 1-methoxy-1-(1,2,2,2-tetrachloroethyl)-3-(2-fluorophenyl) urea | Cl F | 40.6 5.4 | 40.2 5.8 | | | | | 75–78 |
| 1-methyl-1-(1-fluoro-2,2,2-trichloroethyl)-3-(3,4-dichlorophenyl) urea | Cl F | 48.1 5.1 | 43.8 5.5 | | | | | 100–102 |
| 1-methyl-1-(1-fluoro-2,2,2-trichloroethyl)-3-phenyl urea | Cl F | 35.5 6.3 | 35.5 5.7 | | | | | 152–153 |
| 1-methyl-1-(1-fluoro-2,2,2-trichloroethyl)-3-(3,5-dimethylphenyl) urea | Cl F | 32.5 5.8 | 32.3 4.2 | | | | | 160–162 |
| 1-methyl-1-(1-fluoro-2,2,2-trichloroethyl)-3-(3-chlorophenyl) urea | Cl F | 42.4 5.7 | 39.5 6.1 | | | | | 132–134 |

[1] phosphorus
[2] carbon analysis
[3] analysis for total halogen in milliequivalents per gram
[4] analysis for active halogen (i.e., the halogen on the carbon adjacent to the 1-nitrogen atom)

TABLE II

| Compound | Herbicidal Effectiveness Pre/Post | | | | | |
|---|---|---|---|---|---|---|
| | O | W | C | M | P | L |
| 1-methyl-1-(1-ethoxy-2,2,2-trichloroethyl)-3-(2-fluorophenyl) urea | — | — | — | 93/85 | 100/85 | 100/90 |
| 1-methyl-1-(1-ethoxy-2,2,2-trichloroethyl)-3-(2-trifluoromethylphenyl) urea | — | — | — | 85/100 | 80/98 | 90/60 |
| 1-methyl-1-(1-methoxy-2,2,2-trichloroethyl)-3-(3-tolyl) urea | — | 80/— | — | — | — | 100/— |
| 1-methyl-1-(1-ethoxy-2,2,2-trichloroethyl)-3-(3-chlorophenyl) urea | — | — | — | —/100 | 75/95 | 75/100 |
| 1-methyl-1-(1-methoxy-2,2,2-trichloroethyl)-3-(2-fluorophenyl) urea | — | — | 90/— | 70/— | 85/100 | —/95 |
| 1-methyl-1-(1-methylthio-2,2,2-trichloroethyl)-3-(2- | | | | | | |

TABLE II-continued

| Compound | Herbicidal Effectiveness Pre/Post | | | | | |
|---|---|---|---|---|---|---|
| | O | W | C | M | P | L |
| fluorophenyl) urea | 100/100 | 100/100 | 100/95 | 100/100 | 100/100 | 100/100 |
| 1-methyl-1-(1-ethylthio-2,2,2-trichloroethyl)-3-(2-fluorophenyl) urea | 100/— | 100/— | 100/— | 100/95 | 100/— | 100/90 |
| 1-methyl-1-(1-phenylthio-2,2,2-trichloroethyl)-3-(2-fluorophenyl) urea | 100/— | — | 85/— | 100/95 | 100/— | 85/75 |
| 1-methyl-1-(1-methylthio-2,2,2-trichloroethyl)-3-(3-tolyl) urea | — | — | — | — | — | 80/90 |
| 1-methyl-1-(1-methylthio-2,2,2-trichloroethyl)-3-(3-chlorophenyl) urea | — | — | — | —/70 | — | —/70 |
| 1-methyl-1-(1-ethylthio-2,2,2-trichloroethyl)-3-(3-chlorophenyl) urea | — | — | — | —/70 | — | — |
| 1-methyl-1-(1-ethylthio-2,2,2-trichloroethyl)-3-(3,4,-dichlorophenyl) urea | —/100 | 94/100 | —/90 | — | — | — |
| 1-methyl-1-(1-methylthio-2,2,2-trichloroethyl)-3-(3,4-dichlorophenyl) urea | — | 75/93 | — | — | — | — |
| 1-methyl-1-(1-ethylthio-2,2,2-trichloroethyl)-3-phenyl urea | — | — | — | 75/— | — | — |
| O,O-diethyl 1-(N-methyl-N-2-fluorophenylcarbamoyl-amino)-2,2,2-trichloroethyl phosphonate | 95/— | — | 90/— | 95/70 | 95— | 95/— |
| O,O-dimethyl 1-(N-methyl-N-3-chlorophenylcarbamoyl-amino)-2,2,2-trichloroethyl phosphonate | —/100 | 100/100 | 100/100 | 100/93 | 100/100 | 100/— |
| O,O-dimethyl 1-[N-(3,4-dichlorophenylcarbamoyl)-N-methylamino]-2,2,2-trichloroethyl phosphonate | —/100 | 75/100 | 80/100 | 80/100 | 90/100 | 85/100 |
| O,O-diethyl 1-[N-(3-chlorophenylcarbamoyl)-N-methylamino]-2,2,2-trichloroethyl phosphonate | 70/100 | 95/100 | 100/100 | 75/100 | 90/100 | 80/100 |
| 1-methyl-1-(1-acetoxy-2,2,2-trichloroethyl)-3-(3,4-dichlorophenyl) urea | — | 100/— | 100/— | 100/100 | 100/100 | 100/100 |
| 1-[N'-(2-fluorophenylcarbamoyl)-N'-methyl]amino-2,2,2-trichlorophenyl-N,N-dimethyldithio carbamate | 90/100 | 95/95 | 100/85 | 100/100 | 100/100 | 100/100 |
| 1-methyl-1-(1-acetoxy-2,2,2-trichloroethyl)-3-(3-chlorophenyl) urea | 75/95 | 100/100 | 90/100 | 95/100 | 90/100 | 95/100 |
| 1-methyl-1-(1-N-methylcarbamoyloxy-2,2,2-trichloroethyl)-3-(3-chlorophenyl) urea | 80/100 | 100/100 | 100/100 | 100/100 | 100/100 | 100/100 |
| 1-methyl-1-(1-isothiocyanato-2,2,2-trichloroethyl)-3-(3,4-dichlorophenyl) urea | — | — | 95/— | 100/100 | 95/90 | 95/100 |
| 1-methyl-1-(1-isothiocyanato-2,2,2-trichloroethyl)-3-(2-fluorophenyl) urea | 85/75 | —/70 | 90/80 | 100/100 | 100/100 | 100/100 |
| N-[1-(N'-3-chlorophenylcarbamoyl-N'-methylamino)-2,2,2-trichloroethyl] O,O-dimethylthiophosphoramide | 100/90 | 100/95 | 100/80 | 100/100 | 100/100 | 100/100 |
| N-[1-(N-3,4-dichlorophenylcarbamoyl-N-methylamino)-2,2,2-trichloroethyl] O,O-dimethylthiophosphoramide | 90/100 | 100/100 | 100/100 | 100/100 | 100/100 | 100/100 |
| 1-methyl-1-(1-carbethoxymethylthio-2,2,2-trichloroethyl)-3-(3-chlorophenyl) urea | 75/— | 85/95 | 100/— | 100/100 | 100/70 | 95/95 |
| 1-methyl-1-(1-carbethoxymethylthio-2,2,2-trichloroethyl)-3-(3,4-dichlorophenyl) urea | 99/100 | 94/100 | 99/100 | — | —/100 | —/80 |
| 1-methyl-1-(1-carbethoxymethylthio-2,2,2-trichloroethyl)-3-(2-fluorophenyl) urea | 100/100 | 100/100 | 95/100 | 100/100 | 100/100 | 100/100 |
| 1-methyl-1-(1-carbethoxymethoxy-2,2,2-trichloroethyl)-3-(3-chlorophenyl) urea | 90/100 | 100/100 | 100/100 | 100/100 | 100/100 | 100/100 |
| 1-methyl-1-(1-carbethoxymethoxy-2,2,2-trichloroethyl)-3-(3,4-dichlorophenyl) urea | —/75 | 90/100 | 100/95 | 100/100 | 100/100 | 100/100 |
| 1-methyl-1-(1-carbethoxymethoxy-2,2,2-trichloroethyl)-3-(2-fluorophenyl) urea | 100/100 | 100/100 | 100/100 | 100/100 | 100/100 | 100/100 |
| O,O-dimethyl S-[1-(N-3-chlorophenylcarbamoyl-N-methylamino)-2,2,2-trichloroethyl]dithiophosphate | — | — | — | —/80 | — | —/75 |
| O,O-diethyl-S-[1-(N-3-chlorophenylcarbamoyl-N-methylamino)-2,2,2-trichloroethyl]dithiophosphate | 70/— | 85/— | — | — | — | — |
| O,O-dimethyl S-[1-(N-3,4-dichlorophenylcarbamoyl-N-methylamino)-2,2,2-trichloroethyl]dithiophosphate | —/73 | —/90 | — | — | — | — |
| O,O-dimethyl S-[1-(N-2-fluorophenylcarbamoyl-N-methylamino)-2,2,2-trichloroethyl]dithiophosphate | 85/— | 75/— | 75/— | 100/— | 100/— | 100/— |
| O,O-diethyl S-[1-(N-3,4-dichlorophenylcarbamoyl-N-methylamino)-2,2,2-trichloroethyl]dithiophosphate | — | — | — | —/70 | — | — |
| O,O-diethyl S-[1-(N-2-fluorophenylcarbamoyl-N-methylamino)-2,2,2-trichloroethyl]dithiophosphate | — | — | — | — | —/70 | — |
| 1-methyl-1-(1-iosthiocyanato-2,2,2-trichloroethyl)-3-cyclohexyl urea | 95/— | 100/— | 100/— | 100/95 | 100/— | 100/— |
| 1-methyl-1-(1-isothiocyanato-2,2,2-trichloroethyl)-3-cyclopentyl urea | — | 90/— | 90/— | 100/— | 100/— | 100/80 |
| 1-methyl-1-(1-isothiocyanato-2,2,2-trichloroethyl)-3-t-butyl urea | — | 90/— | 95/— | —/95 | —/90 | —/95 |
| 1-methyl-1-(1-methylsulfonyl-2,2,2-trichloroethyl)-3-cyclohexyl urea | 80/— | 70/— | — | 95/95 | 95/90 | 95/90 |
| 1-methyl-1-(1-methylsulfonyl-2,2-dichlorovinyl)-3-methyl urea | — | — | — | — | —/70 | —/95 |
| 1-methyl-1-(1-methylsulfonyl-2,2-dichlorovinyl-3-cyclopentyl urea | — | — | — | — | 75/— | 85/— |
| 1-methyl-1-(1-methylsulfonyl-2,2,2-trichloroethyl)-3-t-butyl urea | | 80/— | — | — | — | 75/— |

TABLE II-continued

| Compound | Herbicidal Effectiveness Pre/Post | | | | | |
|---|---|---|---|---|---|---|
| | O | W | C | M | P | L |
| 1-methyl-1-(1,2,2,2-tetrachloroethyl)-3-(2-fluorophenyl) urea | 100/100 | 100/100 | 100/100 | 100/100 | 100/100 | 100/100 |
| 1-methyl-1-(1,2,2,2-tetrachloroethyl)-3-(3,4-dichlorophenyl) urea | 90/100 | 100/100 | 100/100 | 100/100 | 100/100 | 100/100 |
| 1-methyl-1-(1,2,2,2-tetrachloroethyl)-3-(2-chlorophenyl) urea | 90/80 | 97/80 | 93/85 | 100/100 | 100/100 | 100/100 |
| 1-methyl-1-(1,2,2,2-tetrachloroethyl)-3-(4-chlorophenyl) urea | 100/100 | 100/100 | 100/100 | 100/100 | 100/100 | 100/100 |
| 1-methyl-1-(1,2,2,2-tetrachloroethyl)-3-(2,4-dichlorophenyl) urea | 70/70 | 92/85 | 100/75 | 100/100 | 100/100 | 100/100 |
| 1-methyl-1-(1,2,2,2-tetrachloroethyl)-3-(4-bromophenyl) urea | 65/50 | 90/90 | 95/0 | 100/100 | 100/100 | 100/100 |
| 1-methyl-1-(1,2,2,2-tetrachloroethyl)-3-(3-chlorophenyl) urea | 90/70 | 100/85 | 95/60 | 100/100 | 100/100 | 100/100 |
| 1-methyl-1-(1,2,2,2-tetrachloroethyl)-3-phenyl urea | 100/100 | 100/100 | 100/85 | 100/100 | 100/100 | 100/100 |
| 1-methyl-1-(1,2,2,2-tetrachloroethyl)-3-(3-chloro-4-bromophenyl) urea | 50/95 | 80/100 | 100/95 | 99/100 | 100/100 | 100/100 |
| 1-methyl-1-(1-hydroxy-2,2,2-trichloroethyl)-3-(3-chlorophenyl) urea | 85/100 | 95/100 | 95/100 | 90/100 | 90/100 | 90/100 |
| 1-methyl-1-(1,2,2,2-tetrachloroethyl)-3-(2-trifluoromethylphenyl) urea | — | 96/— | 91/— | —/85 | —/90 | —/85 |
| 1-methyl-1-(1,2,2,2-tetrachloroethyl)-3-(3,5-dichlorophenyl) urea | — | — | — | 100/80 | 100/— | 100/70 |
| 1-methyl-1-(2-bromo-1,2,2-trichloroethyl)-3-(2-fluorophenyl urea | 100/100 | 100/100 | 100/100 | 100/100 | 100/100 | 100/100 |
| 1-methyl-1-(1-bromo-1,2,2-trichloroethyl)-3-(2-fluorophenyl) urea | 100/100 | 100/100 | 100/100 | 100/100 | 100/100 | 100/100 |
| 1-methyl-1-(1,2,2,2-tetrachloroethyl)-3-(4-methoxyphenyl) urea | 90/— | 100/— | 100/— | 95/100 | 95/95 | 95/100 |
| 1-methyl-1-(2-bromo-1,2,2-trichloroethyl)-3-(3,4-dichlorophenyl) urea | 70/95 | 95/100 | —/100 | 95/100 | 95/100 | 95/100 |
| 1-methyl-1-(2-bromo-1,2,2-trichloroethyl)-3-(3-chlorophenyl) urea | 100/100 | 100/100 | 100/85 | 100/100 | 100/100 | 100/100 |
| 1-methyl-1-(1,2,2,2-tetrachloroethyl)-3-(3-trifluoromethylphenyl) urea | 90/90 | 100/100 | 100/95 | 95/100 | 95/100 | 100/100 |
| 1-methyl-1-(1,2-dibromo-2,2-dichloroethyl)-3-(2-fluorophenyl) urea | —/100 | —/100 | —/100 | —/100 | —/100 | —/100 |
| 1-methyl-1-(1,2,2,2-tetrachloroethyl)-3-[3-methyl-4-(4'-chlorophenylthio)phenyl] urea | — | — | — | —/100 | —/100 | —/100 |
| 1-methyl-1-(1,2,2,2-tetrachloroethyl)-3-[3-methyl-4-(4'-chlorophenylsulfonyl)phenyl] urea | — | — | — | —/100 | —/90 | —/95 |
| 1-methyl-1-(1,2,2-trichloroethyl)-3-(3-chlorophenyl) urea | 100/100 | 100/100 | 100/100 | 100/100 | 100/100 | 100/100 |
| 1-methyl-1-(1,2,2,2-tetrachloroethyl)-3-(4-phenoxyphenyl) urea | 90/— | 95/— | 100/— | 100/100 | 100/100 | 100/100 |
| 1-methyl-1-(1,2,2,2-tetrachloroethyl)-3-[4-(4'-chlorophenoxy)phenyl] urea | — | — | — | 90/— | 100/100 | 100/100 |
| 1-methyl-1-(1-hydroxy-2,2,2-trichloroethyl)-3-(3-pyridyl) urea | 90/— | 90/— | 95/— | — | — | —/90 |
| 1-methyl-1-(1-hydroxy-2,2,2-trichloroethyl)-3-(2-thiazolyl) urea | 85/— | 90/— | 85/— | 95/100 | 100/90 | 100/100 |
| 1-methyl-1-(1-hydroxy-2,2,2-trichloroethyl)-3-2-pyridyl) urea | —/95 | 80/95 | —/90 | —/100 | 70/100 | 90/100 |
| 1-methyl-1-(1-hydroxy-2,2,2-trichloroethyl)-3-(2-pyrimidyl) urea | 70/— | 90/— | 90/— | — | —/70 | — |
| 1-methyl-1-(1,2,2,2-tetrachloroethyl)-3-cyclopentyl urea | — | 95/— | 95/90 | 95/100 | 100/95 | 100/100 |
| 1-methyl-1-(1,2,2,2-tetrachloroethyl)-3-cyclohexyl urea | 100/90 | 95/85 | 95/— | 100/100 | 100/95 | 100/100 |
| 1-methyl-1-(1,2,2,2-tetrachloroethyl)-3-methyl urea | 80/— | 90/— | 90/— | — | 90/— | 70/— |
| 1-methyl-1-(1,2,2,2-tetrachloroethyl)-3-n-hexyl urea | — | — | — | —/100 | —/95 | —/95 |
| 1-methyl-1-(1,2,2,2-tetrachloroethyl)-3-t-butyl urea | 90/— | 90/— | 90/— | 70/— | — | — |
| 1-methyl-1-(1,2,2,2-tetrachloroethyl)-3-n-dodecyl urea | 80/— | 90/— | 90/— | —/70 | 95/80 | 100/80 |
| *1-methyl-1-(1-fluoro-2,2,2-trichloroethyl)-3-(3,4-dichlorophenyl) urea | 20/30 | 85/30 | 95/95 | 95/90 | 99/90 | 99/100 |
| *1-methyl-1-(1-fluoro-2,2,2-trichloroethyl)-3-phenyl urea | 98/75 | 98/45 | 98/45 | 100/90 | 100/95 | 98/95 |
| *1-methyl-1-(1-fluoro-2,2,2-trichloroethyl)-3-(3,5-dimethylphenyl) urea | 85/0 | 98/0 | 98/0 | 100/10 | 100/10 | 100/0 |
| *1-methyl-1-(1-fluoro-2,2,2-trichloroethyl)-3-(3-chlorophenyl) urea | 90/0 | 99/95 | 100/75 | 100/100 | 100/100 | 100/100 |

*tested at 33 micrograms/cm$^2$

TABLE III

| (Comparison of compound of the present invention with prior art compound) | | | | | | |
|---|---|---|---|---|---|---|
| | O | W | C | M | P | L |
| 1-methyl-1-(1-hydroxy-2,2,2-trichloroethyl)-3-(3-chlorophenyl) urea | 85/100 | 95/100 | 95/100 | 90/100 | 90/100 | 90/100 |

TABLE III-continued

| (Comparison of compound of the present invention with prior art compound) | O | W | C | M | P | L |
|---|---|---|---|---|---|---|
| 1-(1-hydroxy-2,2,2-trichloroethyl)-3-(3-chlorophenyl) urea. | 0/60 | 0/90 | 0/90 | 10/35 | 35/40 | 30/40 |

Tables II and III:
O = Wild Oats (*Avena fatua*)
W = Watergrass (*Echinochloa crusgalli*)
C = Crabgrass (*Digitaria sanguinalis*)
M = Mustard (*Brassica arvensis*)
P = Pigweed (*Amaranthus retroflexus*)
L = Lambsquarter (*Cheropodium album*)

What is claimed is:

1. A compound of the formula

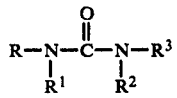

wherein R is an aromatic hydrocarbyl group of 6 to 12 carbon atoms substituted with 0 to 5 halogen atoms of atomic number 9 to 35 (fluorine, chlorine or bromine), nitro, alkyl of 1 to 4 carbon atoms, alkoxy of 1 to 4 carbon atoms, alkylthio of 1 to 4 carbon atoms, or 0 to 1 alkylsulfoxy of 1 to 4 carbon atoms, alkylsulfonyl of 1 to 4 carbon atoms, trifluoromethyl, phenoxy, phenylthio, phenylsulfoxy, phenylsulfonyl, the phenoxy, phenylthio, phenylsulfoxy or phenylsulfonyl being substituted on the aromatic nucleus with 0 to 5 halogens of atomic number 9 to 35 or alkyl of 1 to 4 carbon atoms; $R^1$ is hydrogen or alkyl of 1 to 4 carbon atoms, $R^2$ is alkyl of 1 to 4 carbon atoms or alkoxy of 1 to 4 carbon atoms and $R^3$ is

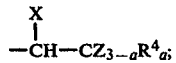

wherein a is 0 to 1 and $R^4$ is hydrogen or $CW'_3$, $W'$ representing hydrogen or halogen of atomic number 9 to 35, Z is halogen of atomic number 9 to 35, and X is

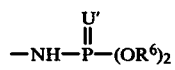

wherein U' is O or S, and $R^6$ is alkyl of 1 to 4 carbon atoms.

2. A compound of claim 1 wherein R is phenyl substituted with 0 to 5 halogen atoms of atomic number 9 to 35, nitro, alkyl of 1 to 4 carbon atoms, alkoxy of 1 to 4 carbon atoms, alkylthio of 1 to 4 carbon atoms or 0 to 1 alkylsulfoxy of 1 to 4 carbon atoms, alkylsulfonyl of 1 to 4 carbon atoms, trifluoromethyl, phenoxy, phenylthio, phenylsulfoxy, phenylsulfonyl, the phenoxy, phenylthio, phenylsulfoxy or phenylsulfonyl being substituted on the aromatic nucleus with 0 to 5 halogen atoms of atomic number 9 to 35.

3. A compound of claim 1 wherein R is phenyl or phenyl substituted with 1 to 2 halogens of atomic number 9 to 35, alkyl of 1 to 2 carbon atoms, alkoxy of 1 to 2 carbon atoms or 1 trifluoromethyl.

4. A compound of claim 3 wherein a is 0 and Z is chlorine or bromine.

5. An herbicidal composition comprising an herbicidally effective amount of the compound of claim 1 and a biologically inert carrier.

6. A method for controlling the growth of undesirable vegetation which comrises applying an herbicidally effective amount of the compound of claim 1 to the vegetation or the growth medium of the vegetation.

7. A method for controlling the growth of undesirable vegetation which comprises applying an herbicidally effective amount of the compound of claim 3 to the vegetation or the growth medium of the vegetation.

8. The compound according to claim 4 which is N-[1-(N-3,4-dichlorophenyl carbamoyl-N-methylamino)-2,2,2-trichloroethyl] O,O-dimethylthiophosphoramide.

9. The compound according to claim 4 which is N-[1-($N^1$-3-chlorophenyl carbamoyl $N^1$-methylamino)-2,2,2-trichloroethyl] O,O-dimethylthiophosphoramide.

* * * * *